United States Patent [19]

Maurer

[11] Patent Number: 4,581,175

[45] Date of Patent: Apr. 8, 1986

[54] N'-ACYLHYDRAZINE-N-THIOCARBOXY-LIC ACID O-CARBAMOYLMETHYL ESTERS

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 684,639

[22] Filed: Dec. 21, 1984

[30] Foreign Application Priority Data

Jan. 4, 1984 [DE] Fed. Rep. of Germany ....... 3400169

[51] Int. Cl.$^4$ ............................................ C07C 155/02
[52] U.S. Cl. ............................. 558/233; 260/239 BF; 546/205; 546/206; 546/226; 546/245; 546/19; 546/164; 546/166; 548/540; 544/160; 544/386
[58] Field of Search ........................ 260/455 A, 455 R

[56] References Cited

U.S. PATENT DOCUMENTS

3,975,419 8/1976 Faucher ......................... 260/455 A

Primary Examiner—Henry R. Jiles
Assistant Examiner—Robert C. Whittenbaugh
Attorney, Agent, or Firm—Sprung Horn Kramer & Woods

[57] ABSTRACT

N'-Acylhydrazine-N-thiocarboxylic acid O-carbamoylmethyl esters of the formula $$R^1-CO-NH-NH-\underset{\underset{S}{\|}}{C}-O-CH_2-CO-N\diagup^{R^2}_{\diagdown R^3}$$

in which $R^1$ is alkyl, alkoxy, alkylthio, halogenoalkyl, aralkyl, aralkoxy, aralkylthio or optionally substituted aryl, and $R^2$ and $R^3$ each independently is hydrogen, alkyl, alkenyl, alkinyl, optionally substituted cycloalkyl or cycloalkenyl, halogenoalkyl, alkoxyalkyl, alkoxy, aralkyl or optionally substituted aryl, or $R^2$ and $R^3$, together with the nitrogen atom to which they are bonded, are an optionally substituted heterocyclic radical, are new compounds useful in preparing known thiadiazole herbicides in high yield by ring closure.

7 Claims, No Drawings

N'-ACYLHYDRAZINE-N-THIOCARBOXYLIC ACID O-CARBAMOYLMETHYL ESTERS

The invention relates to new N'-acylhydrazine-N-thiocarboxylic acid O-carbamoylmethyl esters, several processes for their preparation and their use as intermediates for the synthesis of 1,3,4-thiadiazolyloxyacetamides, which have herbicidal properties.

It is already known that herbicidal heteroaryloxyacetamides are obtained when 2-halogenoheteroaromatics are reacted with hydroxyacetamides (compare, for example, DE-OS (German Published Specification) No. 2,914,003 and DE-OS (German Published Specification) No. 3,004,326 [=European Pat. No. 18,497]; DE-OS (German Published Specification) No. 2,946,526 [=European Pat. No. 29,171] and U.S. application Ser. No. 490,900, filed May 2, 1983, now pending).

However, in the case of the 1,3,4-thiadiazol-2-yl-oxyacetamides in particular, the desired herbicidal end products are obtained only in an unsatisfactory yield and purity when 2-halogeno-1,3,4-thiadiazoles are used as the starting substances.

New N'-acylhydrazine-N-thiocarboxylic acid O-carbamoylmethyl esters of the general formula (I)

$$R^1-CO-NH-NH-\underset{\underset{S}{\|}}{C}-O-CH_2-CO-N\diagup^{R^2}_{\diagdown R^3} \quad (I)$$

in which
$R^1$ represents alkyl, alkoxy, alkylthio, halogenoalkyl, aralkyl, aralkoxy, aralkylthio or optionally substituted aryl and
$R^2$ and $R^3$ independently of one another represent hydrogen, alkyl, alkenyl, alkinyl, in each case optionally substituted cycloalkyl or cycloalkenyl, halogenoalkyl, alkoxyalkyl, alkoxy, aralkyl or optionally substituted aryl, or
$R^2$ and $R^3$, together with the nitrogen atom to which they are bonded, represent an optionally substituted, saturated or unsaturated heterocyclic radical which can contain further hetero-atoms,
have been found.

It has furthermore been found that the new N'-acylhydrazine-N-thiocarboxylic acid O-carbamoylmethyl esters of the general formula (I)

$$R^1-CO-NH-NH-\underset{\underset{S}{\|}}{C}-O-CH_2-CO-N\diagup^{R^2}_{\diagdown R^3} \quad (I)$$

in which
$R^1$ represents alkyl, alkoxy, alkylthio, halogenoalkyl, aralkyl, aralkoxy, aralkylthio or optionally substituted aryl and
$R^2$ and $R^3$ independently of one another represent hydrogen, alkyl, alkenyl, alkinyl, optionally substituted cycloalkyl or cycloalkenyl, halogenoalkyl, alkoxyalkyl, alkoxy, aralkyl or optionally substituted aryl, or
$R^2$ and $R^3$, together with the nitrogen atom to which they are bonded, represent an optionally substituted, saturated or unsaturated heterocyclic radical which can contain further hetero-atoms, are obtained by a process in which
(a) hydrazine-N-thiocarboxylic acid O-carbamoylmethyl esters of the general formula (II)

$$H_2N-NH-\underset{\underset{S}{\|}}{C}-O-CH_2-CO-N\diagup^{R^2}_{\diagdown R^3} \quad (II)$$

in which
$R^2$ and $R^3$ have the abovementioned meanings, are reacted with acylating agents of the formula (III)

$$R^1-CO-X \quad (III)$$

in which
$R^1$ has the abovementioned meaning and
X represents halogen or alkoxy,
if appropriate in the presence of a diluent and if appropriate in the presence of an acid-binding agent, or in which
(b) O-carbamoylmethyl S-carboxymethyl dithiocarbonates of the formula (IV)

$$HO-CO-CH_2-S-\underset{\underset{S}{\|}}{C}-O-CH_2-CO-N\diagup^{R^2}_{\diagdown R^3} \quad (IV)$$

in which
$R^2$ and $R^3$ have the abovementioned meanings, are reacted with N-acylhydrazines of the formula (V)

$$R^1-CO-NH-NH_2 \quad (V)$$

in which
$R^1$ has the abovementioned meaning, if appropriate in the presence of a diluent and if appropriate in the presence of an acid-binding agent, or in which
(c) hydroxyacetamides of the formula (VI)

$$HO-CH_2-CO-N\diagup^{R^2}_{\diagdown R^3} \quad (VI)$$

in which
$R^2$ and $R^3$ have the abovementioned meanings, are reacted successively in a "one-pot process" first with carbon disulphide in the presence of a base and then with an alkali metal chloroacetate, and finally with an N-acylhydrazine of the formula (V)

$$R^1-CO-NH-NH_2 \quad (V)$$

in which $R^1$ has the abovementioned meaning, is appropriate in the presence of a diluent.

Finally, it has been found that the new N'-acylhydrazine-N-thiocarboxylic acid O-carbamoylmethyl esters of the formula (I) are useful intermediates for the preparation of plant protection agents which have herbicidal properties.

Surprisingly, if the new N'-acylhydrazine-N-thiocarboxylic acid O-carbamoylmethyl esters of the formula (I) are used as starting substances, herbicidal 1,3,4-thiadiazol-2-yloxyacetamides are obtained in considerably better yields and a higher purity than when the 2-halogeno-1,3,4-thiadiazoles known from the prior art are used as starting substances.

Formula (I) provides a general definition of the N'-acylhydrazine-N-thiocarboxylic acid O-carbamoylmethyl esters according to the invention.

Preferred compounds of the formula (I) are those in which $R^1$ represents straight-chain or branched alkyl, alkoxy, or alkylthio with in each case 1 to 6 carbon atoms, halogenoalkyl with 1 to 6 carbon atoms and 1 to 13 halogen atoms, in particular fluorine, chlorine and bromine, aralkyl, aralkoxy or aralkylthio with 6 to 10 carbon atoms in the aryl part and 1 or 2 carbon atoms in the alkyl part, or aryl which has 6 to 10 carbon atoms and is optionally mono- or poly-substituted by identical or different substituents, possible substituents being: alkyl and alkoxy with in each case 1 to 4 carbon atoms and halogenoalkyl with 1 to 4 carbon atoms and 1 to 5 halogen atoms, in particular fluorine, chlorine or bromine, and $R^2$ and $R^3$ independently of one another represent hydrogen, straight-chain or branched alkyl with 1 to 8 carbon atoms, straight-chain or branched alkenyl or alkinyl with in each case 2 to 8 carbon atoms, cycloalkyl or cycloalkenyl with in each case 3 to 7 carbon atoms and in each case optionally mono- or poly-substituted by identical or different substituents, possible substituents being, in particular, alkyl radicals with 1 to 4 carbon atoms, straight-chain or branched alkoxy or alkoxyalkyl with 1 to 8 carbon atoms, halogenoalkyl with 1 to 8 carbon atoms and 1 to 5 halogen atoms, in particular fluorine, chlorine and bromine, aralkyl with 6 to 10 carbon atoms in the aryl part and 1 or 2 carbon atoms in the alkyl part, or aryl which has 6 to 10 carbon atoms and is optionally mono- or poly-substituted by identical or different substituents, possible substituents being: halogen, straight-chain or branched alkyl, alkoxy and alkylthio with in each case 1 to 4 carbon atoms, halogenoalkyl, halogenoalkoxy and halogenoalkylthio with in each case 1 or 2 carbon atoms and 1 to 5 halogen atoms, in particular fluorine, chlorine or bromine, and nitro, or $R^2$ and $R^3$, together with the nitrogen atom to which they are bonded, represent a saturated or unsaturated, 5-membered to 7-membered heterocyclic radical which is optionally mono- or poly-substituted by identical or different substituents and can contain up to 2 further hetero-atoms, in particular nitrogen and oxygen, possible substituents being: straight-chain or branched alkyl with 1 to 6 carbon atoms, also in the form of a fused-on ring system, aryl with 6 to 10 carbon atoms, also in the form of a fused-one ring system, or dioxyalkylene with 2 or 3 carbon atoms.

Particularly preferred compounds of the formula (I) are those in which $R^1$ represents straight-chain or branched alkyl, alkoxy or alkylthio with in each case 1 to 4 carbon atoms, halogenoalkyl with 1 to 4 carbon atoms and 1 to 9 identical or different halogen atoms, in particular fluorine, chlorine or bromine, benzyl, benzylthio or phenyl which is optionally mono-, di- or tri-substituted by identical or different substituents, particularly preferred substituents being: methyl, methoxy and trifluoromethyl, and $R^2$ and $R^3$ independently of one another represent hydrogen, straight-chain or branched alkyl with 1 to 6 carbon atoms, straight-chain or branched alkenyl or alkinyl with in each case 2 to 6 carbon atoms, cycloalkyl or cycloalkenyl which has 5 to 7 carbon atoms and is optionally mono-, di- or trisubstituted by identical or different substituents from the group comprising methyl and ethyl, halogenoalkyl with 1 to 6 carbon atoms and 1 to 5 halogen atoms, in particular fluorine, bromine and chlorine; benzyl or for phenyl which are optionally mono-, di- or tri-substituted by identical or different substituents, particularly preferred substituents being: methyl, ethyl, methoxy, methylthio, trifluoromethyl, trifluoromethoxy, trifluoromethylthio, fluorine, chlorine and nitro, or $R^2$ and $R^3$, together with the nitrogen atom to which they are bonded, represent one of the following heterocyclic radicals, which is optionally mono-, di- or tri-substituted by identical or different substitutents:

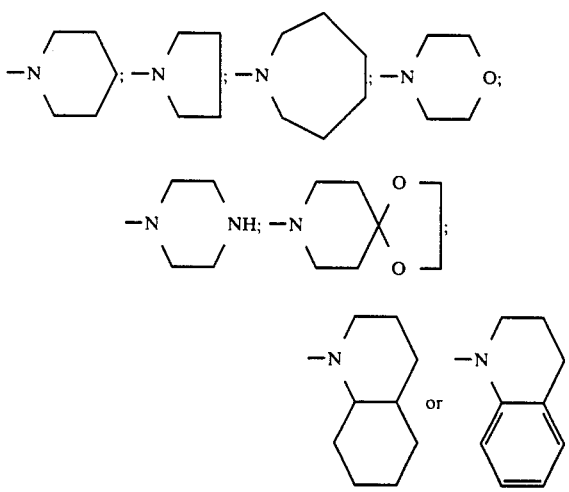

particularly preferred substituents being: methyl, ethyl and phenyl.

The following compounds of the general formula (I) may be mentioned specifically, in addition to the compounds mentioned in the preparation examples:

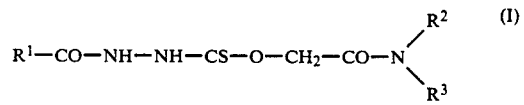

TABLE 1

| $R^1$ | $R^2$ | $R^3$ |
|---|---|---|
| $F_3C-$ | $C_2H_5$ | $C_2H_5-$ |
| $F_3C-$ | $C_2H_5$ | $C_2H_5-$ |
| $F_3C-$ | $n\text{-}C_3H_7$ | $n\text{-}C_3H_7$ |
| $F_3C-$ | $-CH_2-CH=CH_2$ | $-CH_2-CH=CH_2$ |
| $F_3C-$ | $-CH_2-CH_2-CH_2-CH_2-CH_2-$ | |
| $F_3C-$ | $-OCH_3$ | $-CH\begin{smallmatrix}CH_3\\C_2H_5\end{smallmatrix}$ |
| $F_3C-$ | $-CH(CH_3)-CH_2-CH_2-CH_2-CH_2$ | |
| $F_3C-$ | $-CH(C_2H_5)-CH_2-CH_2-CH_2-CH_2-$ | |

TABLE 1-continued

| R¹ | R² | R³ |
|---|---|---|
| F₂ClC— | CH₃ | C₆H₅ |
| F₂ClC— | C₂H₅ | C₂H₅ |
| F₂ClC— | n-C₃H₇ | n-C₃H₇ |
| F₂ClC— | —CH₂—CH=CH₂ | —CH₂—CH=CH₂ |
| F₂ClC— | —CH₂—CH₂—CH₂—CH₂—CH₂— | |
| F₂ClC— | —CH(CH₃)—CH₂—CH₂—CH₂—CH₂— | |
| F₂ClC— | —CH(C₂H₅)—CH₂—CH₂—CH₂—CH₂— | |
| Cl₂FC— | CH₃ | C₆H₅ |
| Cl₂FC— | C₂H₅ | C₆H₅ |
| Cl₂FC— | n-C₃H₇ | n-C₃H₇ |
| Cl₂FC— | CH₂=CH—CH₂— | CH₂=CH—CH₂— |
| Cl₂FC— | C₂H₅ | C₂H₅ |
| Cl₂FC— | —CH(CH₃)—CH₂—CH₂—CH₂—CH₂— | |
| Cl₂FC— | —CH₂—CH₂—CH₂—CH₂—CH₂— | |
| Cl₂FC— | —CH(C₂H₅)—CH₂—CH₂—CH₂—CH₂— | |
| Cl₃C— | CH₃ | C₆H₅— |
| Cl₃C— | C₂H₅ | C₆H₅— |
| Cl₃C— | C₂H₅ | C₂H₅— |
| Cl₃C— | CH₂=CH—CH₂— | CH₂=CH—CH₂— |
| Cl₃C— | —CH₂—CH₂—CH₂—CH₂—CH₂— | |
| Cl₃C— | —CH(CH₃)—CH₂—CH₂—CH₂—CH₂— | |
| Cl₃C— | —CH(C₂H₅)—CH₂—CH₂—CH₂—CH₂— | |
| CH₃— | CH₃ | C₆H₅ |
| CH₃— | C₂H₅ | C₆H₅ |
| CH₃— | C₂H₅ | C₂H₅ |
| CH₃— | n-C₃H₇ | n-C₃H₇ |
| CH₃— | CH₂=CH—CH₂— | CH₂=CH—CH₂— |
| CH₃— | —CH₂—CH₂—CH₂—CH₂—CH₂— | |
| CH₃— | —CH₂—CH₂—O—CH₂—CH₂— | |
| CH₃— | —CH(CH₃)—CH₂—CH₂—CH₂—CH₂— | |
| CH₃— | —CH(C₂H₅)—CH₂—CH₂—CH₂—CH₂— | |
| C₂H₅ | CH₃ | C₆H₅ |
| C₂H₅ | C₂H₅ | C₆H₅ |
| C₂H₅ | C₂H₅ | C₂H₅ |
| C₂H₅ | n-C₃H₇ | n-C₃H₇ |
| CH₃—(CH₂)₂— | CH₃ | C₆H₅ |
| CH₃—(CH₂)₂— | n-C₃H₇ | n-C₃H₇ |
| CH₃—(CH₂)₂— | CH₂=CH—CH₂— | CH₂=CH—CH₂— |
| CH₃—(CH₂)₂— | C₂H₅ | C₂H₅ |
| CH₃—(CH₂)₂— | C₂H₅ | C₆H₅ |
| CH₃—(CH₂)₂— | —CH₂—CH₂—CH₂—CH₂—CH₂— | |
| CH₃—(CH₂)₂— | —CH(C₂H₅)—CH₂—CH₂—CH₂—CH₂— | |
| (CH₃)₂CH— | CH₃ | C₆H₅ |
| (CH₃)₂CH— | C₂H₅ | C₆H₅ |
| (CH₃)₂CH— | C₂H₅ | C₂H₅ |
| (CH₃)₂CH— | n-C₃H₇ | n-C₃H₇ |
| (CH₃)₂CH— | CH₂=CH—CH₂— | CH₂=CH—CH₂— |
| (CH₃)₂CH— | HC≡C—CH₂— | HC≡C—CH₂— |
| (CH₃)₂CH— | —CH₂—CH₂—CH₂—CH₂—CH₂— | |
| (CH₃)₂CH— | —CH(CH₃)—CH₂—CH₂—CH₂—CH₂— | |
| (CH₃)₂CH— | —CH(C₂H₅)—CH₂—CH₂—CH₂—CH₂— | |
| ClH₂C— | CH₃ | C₆H₅ |
| ClH₂C— | CH₂=CH—CH₂— | CH₂=CH—CH₂— |
| ClH₂C— | n-C₃H₇ | n-C₃H₇ |
| ClH₂C— | —CH(C₂H₅)—CH₂—CH₂—CH₂—CH₂— | |
| Cl₂HC— | CH₃ | C₆H₅ |
| Cl₂HC— | C₂H₅ | C₂H₅ |
| Cl₂HC— | n-C₃H₇ | n-C₃H₇ |
| Cl₂HC— | CH₂=CH—CH₂— | CH₂=CH—CH₂— |
| F₂HC— | —CH₂—CH₂—CH₂—CH₂—CH₂— | |
| F₂HC— | CH₃ | C₆H₅ |
| F₂HC— | —CH(C₂H₅)—CH₂—CH₂—CH₂—CH₂— | |
| F₂HC— | n-C₃H₇ | n-C₃H₇ |
| FH₂C— | CH₂=CH—CH₂— | CH₂=CH—CH₂— |
| FH₂C— | CH₃ | C₆H₅ |
| FH₂C— | C₂H₅ | C₆H₅ |
| FH₂C— | n-C₃H₇ | n-C₃H₇ |
| F₃C—CF₂—CF₂— | CH₃ | C₆H₅ |
| F₃C—CF₂—CF₂— | n-C₃H₇ | n-C₃H₇ |
| F₃C—CF₂—CF₂— | CH₂=CH—CH₂— | CH₂=CH—CH₂— |
| F₃C—CF₂—CF₂— | —CH(C₂H₅)—CH₂—CH₂—CH₂—CH₂— | |
| FClHC— | CH₃ | C₆H₅ |
| FClHC— | n-C₃H₇ | n-C₃H₇ |
| FClHC— | CH₂=CH—CH₂— | CH₂=CH—CH₂— |
| FClHC— | —CH₂—CH₂—CH₂—CH₂—CH₂— | |
| FClHC— | —CH(CH₃)—CH₂—CH₂—CH₂—CH₂— | |
| C₆H₅ | CH₃ | C₆H₅ |
| C₆H₅ | C₂H₅ | C₆H₅ |
| C₆H₅ | n-C₃H₇ | n-C₃H₇ |
| C₆H₅ | CH₂=CH—CH₂— | CH₂=CH—CH₂— |
| C₆H₅ | —CH₂—CH₂—CH₂—CH₂—CH₂— | |

If, for example, O-(N-methyl-N-phenylcarbamoylmethyl)hydrazinethiocarboxylate and ethyl trifluoroacetate are used, the course of the reaction in process (a) according to the invention can be represented by the following equation:

$$F_3C-CO-OC_2H_5 + H_2N-NH-CS-O-CH_2-CO-N\begin{matrix}CH_3\\C_6H_5\end{matrix} \xrightarrow[\text{(Base)}]{-C_2H_5OH}$$

-continued

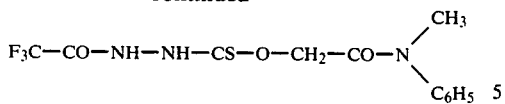

If, for example, S-carboxymethyl O-(N-methyl-N-phenylcarbamoylmethyl)dithiocarbonate and N-acetylhydrazine are used as starting substances, the course of reaction in process (b) according to the invention can be represented by the following equation:

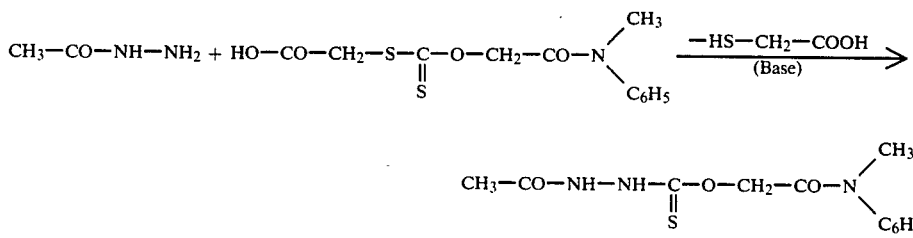

If, for example, glycollic acid piperidide, carbon disulphide, potassium hydroxide, sodium chloroacetate and N-acetylhydrazine are used as starting substances, the course of reaction in process (c) according to the invention can be represented by the following equation:

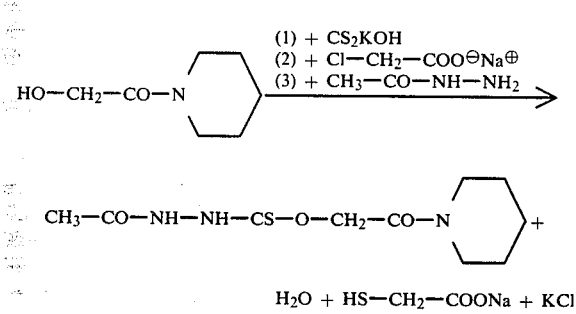

Formula (II) provides a general definition of the hydrazine-thiocarboxylic acid O-carbamoylmethyl esters required as starting substances for process (a) according to the invention. In this formula (II), $R^2$ and $R^3$ preferably represent those radicals which have already been mentioned as preferred for these substituents in the description of the substances of the formula (I) according to the invention.

The hydrazine-thiocarboxylic acid O-carbamoylmethyl esters are not yet known.

They are obtained either by a process in which O-carbamoylmethyl S-carboxymethyl dithiocarbonates of the formula (IV)

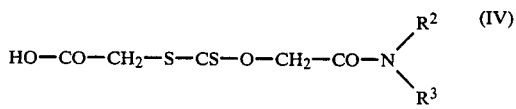

in which
$R^2$ and $R^3$ have the abovementioned meanings, are reacted with hydrazine hydrate, if appropriate in the presence of a diluent, such as, for example, water, and if appropriate in the presence of an acid-binding agent, such as, for example, sodium bicarbonate, at temperatures between $-20°$ C. and $+50°$ C., or by a process in which hydroxyacetamides of the formula (VI)

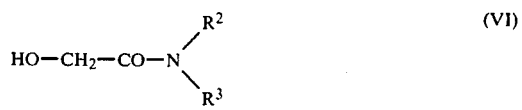

in which
$R^2$ and $R^3$ have the abovementioned meanings, are reacted successively in a "one-pot process" first with

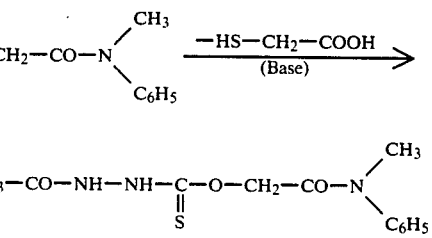

carbon disulphide in the presence of a base, such as, for example, an alkali metal hydroxide, and then with an alkali metal chloroacetate, such as, for example, sodium chloroacetate, and finally with hydrazine hydrate, if appropriate in the presence of a diluent, such as, for example, water, at temperatures between $0°$ C. and $+60°$ C.

This invention likewise relates to the new hydrazine-thiocarboxylic acid O-carbamoyl esters (II) and the processes described above for their preparation.

Formula (III) provides a general definition of the acylating agents also required as starting substances for carrying out process (a) according to the invention. In this formula (III), $R^1$ preferably represents those radicals which have already been mentioned as preferred for this substituent in connection with the description of the substances of the formula (I) according to the invention. X preferably represents chlorine, bromine, methoxy or ethoxy. The acylating agents of the formula (III) are generally known compounds of organic chemistry.

Formula (IV) provides a general definition of the O-carbamoylmethyl S-carboxymethyl dithiocarbonates required as starting substances for carrying out process (b) according to the invention and for the preparation of the precursors of the formula (II). In this formula (IV), $R^2$ and $R^3$ preferably represent those substituents with have already been mentioned as preferred for these radicals in the description of the substances of the formula (I) according to the invention.

The O-carbamoylmethyl S-carboxymethyl dithiocarbonates of the formula (IV) are not yet known.

They are obtained by a process in which hydroxyacetamides of the formula (VI)

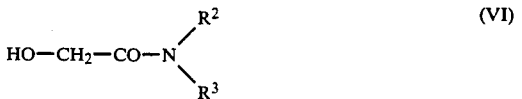

in which $R^2$ and $R^3$ have the abovementioned meanings, are reacted successively, in a "one-pot process", first with carbon disulphide in the presence of a base, such as for example, potassium hydroxide, and then, with an alkali metal chloroacetate, such as, for example, sodium chloroacetate, and finally with an acid, such as, for example, hydrochloric acid, if appropriate in the presence of a diluent, such as, for example, water, at temperatures between 0° C. and +60° C.

Formula (VI) provides a general definition of the hydroxyacetamides required as starting substances for carrying out process (c) according to the invention and for the preparation of the precursors of the formula (IV). In this formula (VI), $R^2$ and $R^3$ preferably represent those radicals which have already been mentioned as preferred for these substituents in the description of the substances of the formula (I) according to the invention.

The hydroxyacetamides of the formula (VI) are known (compare, for example, European Pat. No. 18,497, European Pat. No. 29,171, DE-OS (German Published Specification) No. 3,038,598 and U.S. Pat. No. 4,455,428).

Formula (V) provides a general definition of the N-acylhydrazines also required as starting substances for carrying out processes (b) and (c) according to the invention. In this formula (V), $R^1$ preferably represents those radicals which have already been mentioned as preferred for this substituent in the description of the substances of the formula (I) according to the invention.

The N-acylhydrazines of the formula (V) are generally known compounds of organic chemistry or can be obtained in the generally customary manner by acylation of hydrazine by processes which are known in principle (compare, for example, C. Ferri, 'Reaktionen der organischen Synthese' ('Reactions of Organic Synthesis'), Thieme Verlag Stuttgart 1978, pages 562 and 563).

Possible diluents for carrying out process (a) according to the invention are inert organic solvents. Solvents which are preferably used are aliphatic of aromatic, optionally halogenated hydrocarbons, such as, for example, benzine, benzene, toluene, xylene, chlorobenzene, methylene chloride, chloroform or carbon tetrachloride, ethers, such as diethyl ether, dioxane or tetrahydrofuran, ketones, such as acetone or butanone, nitriles, such as acetonitrile or propionitrile, amides, such as dimethylformamide, hexamethylphosphoric acid triamide or N-methylpyrrolidone, and, if appropriate, also alcohols, such as methanol, ethanol, propanol or butanol.

Possible acid-binding agents in carrying out process (a) according to the invention are all the inorganic or organic bases which can customarily be used. Bases which are preferably used are alkali metal alcoholates, such as, for example, sodium methylate or sodium ethylate, or tertiary amines, such as triethylamine, pyridine, dimethylaminopyridine, diazabicyclononene (DBN) or diazabicycloundecene (DBU).

The reaction temperatures can be varied within a substantial range in carrying out process (a) according to the invention. In general, the reaction is carried out at temperatures between $-20°$ C. and $+60°$ C., preferably between 0° C. and $+30°$ C.

For carrying out process (a) according to the invention, in general 1 to 1.5 moles, preferably equimolar amounts, of acylating agent of the formula (III) and 1 to 1.5 moles, preferably equimolar amounts, of acid-binding agent are employed per mole of hydrazine-thiocarboxylic acid O-carbamoylmethyl ester of the formula II.

For working up, water is added to the reaction mixture, the mixture is neutralized, if excess acid-binding agent is present, and the reaction product of the formula (I), which is insoluble in water, is isolated by filtration.

Possible diluents for carrying out process (b) according to the invention are likewise organic solvents or aqueous systems. Water-miscible solvents, such as, for example, methanol, ethanol or acetonitrile, or mixtures thereof with water, are preferably used. The use of water as the diluent is particularly preferred.

Possible acid-binding agents in carrying out process (b) according to the invention are in principle all the customary inorganic and organic bases. Bases which are preferably used are alkali metal carbonates or bicarbonates, such as, for example, sodium bicarbonate or potassium bicarbonate.

The reaction temperatures can likewise be varied within a substantial range in carrying out process (b) according to the invention. In general, the reaction is carried out at temperatures between $-20°$ C. and $+50°$ C., preferably between 0° C. and $+30°$ C.

For carrying out process (b) according to the invention, in general 1 to 1.3 moles, preferably equimolar amounts, of N-acylhydrazine of the formula (V) and in general 1 to 1.3 moles, preferably equimolar amounts, of acid-binding agents are employed per mole of O-carbamoylmethyl S-carboxymethyldithiocarbonate of the formula (IV). Working up and isolation of the reaction products of the formula (I) are effected as described for process (a).

Possible diluents for carrying out process (c) according to the invention are likewise water-miscible inert organic diluents or aqueous systems. Pure water is preferably used.

Possible bases in carrying out process (c) according to the invention are strong inorganic bases. Bases which are preferably used are alkali metal hydroxides, such as, for example, sodium hydroxide or potassium hydroxide.

The reaction temperatures can likewise be varied within a substantial range in carrying out process (c) according to the invention. In general, the reaction is carried out at temperatures between $-20°$ C. and $+60°$ C., preferably between 0° C. and $+40°$ C.

For carrying out process (c) according to the invention, in general 1 to 1.3 moles of carbon disulphide, 1 to 1.3 moles of alkali metal chloroacetate, such as, for example, sodium chloroacetate, 1 to 1.3 moles of N-acylhydrazine of the formula (V) and 1 to 1.3 moles of base are employed per mole of hydroxyacetamide of the formula (VI), and equimolar amounts of all of the reactants which participate are preferably used. Working up and isolation of the reaction products of the formula (I) are effected as described for process (a).

As already mentioned, the N'-acylhydrazine-N-thiocarboxylic acid O-carbamoylmethyl esters of the formula (I) according to the invention are useful intermediates.

They can be converted into 1,3,4-thiadiazol-2-yl-oxyacetamides of the general formula (VII)

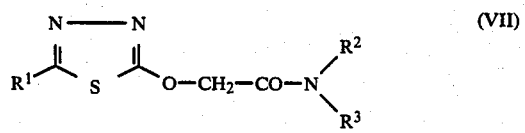

in which $R^1$, $R^2$ and $R^3$ have the abovementioned meanings, by cyclizing the compounds of the formula (I) with a strong acid, such as, for example, concentrated sulphuric acid, at temperatures between −30° C. and +20° C.

The 1,3,4-thiadiazol-2-yloxyacetamides of the formula (VII) have herbicidal properties (compare, for example, DE-OS (German Published Specification) No. 2,914,003, DE-OS (German Published Specification) No. 3,004,326, European Pat. No. 18,497, DE-OS (German Published Specification) No. 2,946,526, European Pat. No. 29,171 and U.S. application Ser. No. 490,0900, filed May 2, 1983, now pending).

PREPARATION EXAMPLES

Example 1

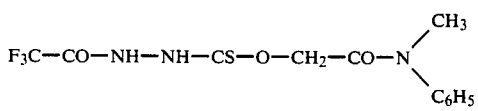

Process a

A solution of 2.8 g (0.052 mole) of sodium methanolate in 20 ml of methanol is first added dropwise to a mixture of 7.1 g (0.05 mole) of ethyl trifluoroacetate and 40 ml of ethanol at 0° C. to 5° C. and, after 15 minutes, 11.95 g (0.05 mole) of O-(N-methyl-N-phenyl-carbamoylmethyl)hydrazinethiocarboxylate are added. The mixture is stirred at 5° C. to 10° C. for one hour and a mixture of 6 ml of concentrated hydrochloric acid and 15 ml of water is then added dropwise. The solvent is subsequently distilled off in vacuo, the residue is stirred with cold water and, after crystallization, the product is filtered off with suction.

14.5 g (87% of theory) of O-(N-methyl-N-phenylcarbamoylmethyl) N'-trifluoroacetyl-hydrazine-N-thiocarboxylate are obtained in this manner in the form of a colorless powder, which has a melting point of 107° C., with decomposition.

PREPARATION OF THE STARTING COMPOUND

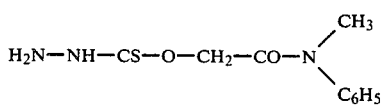

29.9 g (0.1 mole) of S-carboxymethyl O-(N-methyl-N-phenyl-carbamoylmethyl)dithiocarbonate are added in portions to a solution of 9.3 g (0.11 mole) of sodium bicarbonate in 100 ml of water. After one hour, 5 g (0.1 mole) of hydrazine hydrate are added dropwise at 5° C. to 10° C., the mixture is subsequently stirred for one hour, with cooling, and the product which has precipitated is filtered off with suction.

20 g (84% of theory) of O-(N-methyl-N-phenylcarbamoylmethyl)hydrazinethiocarboxylate are obtained in this manner in the form of a beige powder of melting point 104° C.

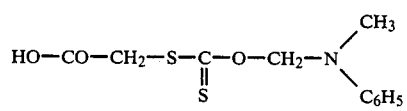

16.5 g (0.1 mole) of glycollic acid N-methylanilide are first added to a solution of 5.6 g (0.1 mole) of potassium hydroxide in 20 ml of water at 10° C., followed by 7.6 g (0.1 mole) of carbon disulphide. The mixture is subsequently stirred at 10° C. to 15° C. for 10 minutes and 11.6 g (0.1 mole) of sodium chloroacetate are then added. The temperature thereby rises up to 32° C. After 1.5 hours, the mixture is diluted with 40 ml of water and brought to pH 2 with concentrated hydrochloric acid. The product which has precipitated is extracted twice with 100 ml of methylene chloride each time and the organic phase is dried over sodium sulphate and evaporated in vacuo.

27.8 g (93% of theory) of S-carboxymethyl O-(N-methyl-N-phenylcarbamoylmethyl)dithiocarbonate are obtained in the form of yellow crystals of melting point 109° C.

EXAMPLE 2

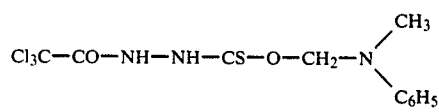

Process a 4 g (0.05 mole) of pyridine are first added to a mixture of 11.95 g (0.05 mole) of O-(N-methyl-N-phenylcarbamoylmethyl)hydrazinethiocarboxylate and 25 ml of N,N-dimethylformaide at 0° C. to 5° C., followed by 9.1 g (0.05 mole) of trichloroacetyl chloride. The mixture is subsequently stirred at 0° C. to 5° C. for half an hour and 100 ml of ice-water are added. After crystallization, the reaction product which has precipitated is filtered off with suction.

14.8 g (77% of theory) of O-(N-methyl-N-phenylcarbamoylmethyl)N'-trichloroacetyl-hydrazine-N-thiocarboxylate are obtained in the form of a colorless powder of melting point 104° C. (decomposition).

EXAMPLE 3

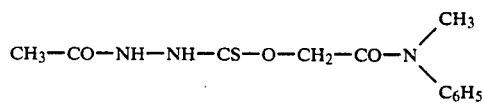

Process b 29.9 g (0.1 mole) of S-carboxymethyl O-(N-methyl-N-phenylcarbamoylmethyl)dithiocarbonate are added in portions to a solution of 8.9 g (0.105 mole) of sodium bicarbonate in 100 mL of water. After half an hour, the undissolved material is filtered off and 13.5 g (0.1 mole) of a 55% strength aqueous acetic hydrazide solution are then added to the filtrate at 0° C. to 10° C. The reaction mixture is subsequently stirred at room temperature for 6 hours and the product which has precipitated is then filtered off with suction.

21.7 g (77% of theory) of O-(N-methyl-N-phenylcarbamoylmethyl)N'-acetyl-hydrazine-N-thiocarboxylate are obtained in this manner in the form of a colorless powder of melting point 115° C.

Process c 8.3 g (0.05 mole) of glycollic acid N-methylanilide are first added to a solution of 2.8 g (0.05 mole) of potassium hydroxide in 10 ml of water at 20° C., and 3.8 g (0.05 mole) of carbon disulphide are then added dropwise at 10° C. to 20° C. After 10 minutes, 5.8 g (0.05 mole) of sodium chloroacetate are added to the reaction mixture. The temperature rises up to about 30° C. After 2 hours, 6.8 g (0.05 mole) of a 55% strength solution of acetic hydrazide in water are added dropwise. The mixture is subsequently stirred at room temperature for 6 hours and 40 ml of cold water are then added; the product which has precipitated is filtered off with suction and rinsed with a little ice-water.

10.8 g (77% of theory) of O-(N-methyl-N-phenylcarbamoylmethyl)N'-acetyl-hydrazine-N-thiocarboxylate are obtained in this manner in the form of a colorless powder of melting point 112° C.

EXAMPLE 4

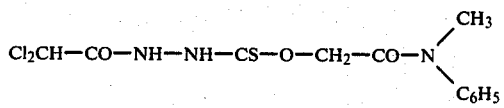

Process a 73,8 g (0,5 mole) of dichloroacetyl chloride are added to a mixture of 119.5 g (0.5 mole) of O-(N-methyl-N-phenylcarbamoylmethyl)hydrazinethiocarboxylate and 180 ml of acetonitrile at 5° to 10° C. The mixture is subsequently stirred at 5° to 10° C. for 2 hours and then added to a solution of 52 g (0.6 mole) of sodium bicarbonate in 1700 ml of water. The product which has precipitated is filtered off with suction after crystallization.

157.5 g (90% of theory) of O-(N-methyl-N-phenylcarbamoylmethyl)N'-dichloroacetyl-hydrazine-N-thiocarboxylate are obtained in the form of a slight yellow powder of melting point 85°–86° C.

EXAMPLE 5

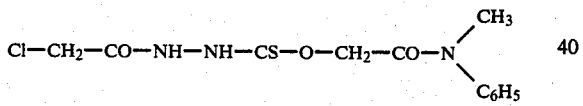

The compound O-(N-methyl-N-phenyl-carbamoylmethyl)N'-chloroacetyl-hydrazine-N-thiocarboxylate can be prepared analogously to Example 4; the product is obtained in the form of a non-crystalline oil.

USE EXAMPLE

Preparation of the secondary products

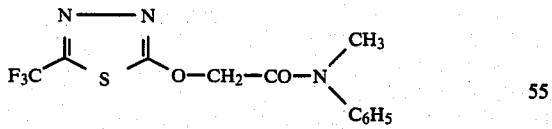

16.8 g (0.05 mole) of O-(N-methyl-N-phenyl-carbamoylmethyl)N'-trifluoroacetyl-hydrazine-N-thiocarboxylate are added to 50 ml of concentrated sulphuric acid at 0° C. to 5° C. The mixture is stirred at 0° C. to 5° C. for one hour, poured into 500 g of ice and then extracted twice by shaking with 100 ml of methylene chloride each time. The organic phase is dried over sodium sulphate and evaporated in vacuo.

12.7 g (80% of theory) of N-methyl-N-phenyl-2-(5-trifluoromethyl-1,3,4-thiadiazol-2-yloxy)-acetamide of melting point 54° C. are obtained.

It will be understood that the specification and examples are illustrative but not limitative of the present invention and that other embodiments within the spirit and scope of the invention will suggest themselves to those skilled in the art.

I claim:

1. An N'-acylhydrazine-N-thiocarboxylic acid O-carbamoyl-methyl ester of the formula

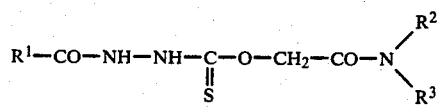

in which
R$^1$ is alkyl, alkoxy or alkylthio with in each case 1 to 6 atoms, halogenalkyl with 1 to 6 carbon atoms and 1 to 13 halogen atoms, aralkyl, aralkoxy or aralkylthio with 6 to 10 carbon atoms in the aryl part and 1 to 2 carbon atoms in the alkyl part, or aryl which has 6 to 10 carbon atoms and is optionally independently substituted by alkyl or alkoxy with in each case 1 to 4 carbon atoms, and/or halogenoalkyl with 1 to 4 carbon atoms and 1 to 5 halogen atoms, or R$^2$ and R$^3$ each independently is hydrogen, alkyl with 1 to 8 carbon atoms, alkenyl or alkinyl with in each case 2 to 8 carbon atoms, cycloalkyl or cycloalkenyl with in each case 3 to 7 carbon atoms and optionally independently substituted by alkyl with 1 to 4 carbon atoms, alkoxy or alkoxyalkyl with 1 to 8 carbon atoms, halogenoalkyl with 1 to 8 carbon atoms and 1 to 5 halogen atoms, aralkyl with 6 to 10 carbon atoms in the aryl part and 1 to 2 carbon atoms in the alkyl part, and/or aryl which has 6 to 10 carbon atoms and is optionally independently substituted by halogen, alkyl, alkoxy or alkylthio with in each case 1 to 4 carbon atoms, halogenoalkyl, halogenoalkoxy or halogenoalkylthio with in each case 1 to 2 carbon atoms and 1 to 5 halogen atoms, or nitro.

2. A compound according to claim 1, in which
R$^1$ is alkyl, alkoxy or alkylthio with in each case 1 to 4 carbon atoms, halogenoalkyl with 1 to 4 carbon atoms and 1 to 9 identical or different halogen atoms, or benzyl, benzylthio or phenyl which is optionally mono-, di- or tri-substituted by methyl, methoxy and/or trifluoromethyl, and R$^2$ and R$^3$ each independently is hydrogen, alkyl with 1 to 6 carbon atoms, alkenyl or alkinyl with in each case 2 to 6 carbon atoms, cycloalkyl or cycloalkenyl which has 5 to 7 carbon atoms and is optionally mono-, di- or tri-substituted by methyl and/or ethyl, halogenoalkyl with 1 to 6 carbon atoms and 1 to 5 halogen atoms, benzyl or phenyl which is optionally mono-, di- or tri-substituted by methyl, ethyl, methoxy, methylthio, trifluoromethyl, trifluoromethoxy, trifluoromethylthio, fluorine, chlorine and/or nitro.

3. A compound according to claim 1, wherein such compound is O-(N-methyl-N-phenyl-carbamoylmethyl)N'-trifluoroacetyl-hydrazine-N-thiocarboxylate of the formula

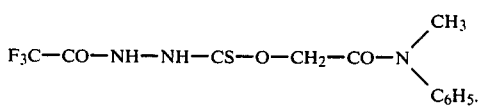

4. A compound according to claim 1, wherein such compound is O-(N-methyl-N-phenyl-carbamoylmethyl)N'-trichloroacetyl-hydrazine-N-thiocarboxylate of the formula

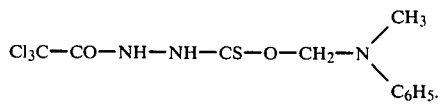

5. A compound according to claim 1, wherein such compound is O-(N-methyl-N-phenyl-carbamoylmethyl)N'-acetylhydrazine-N-thiocarboxylate of the formula

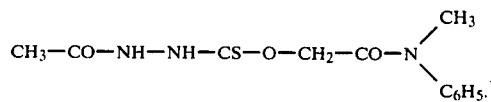

6. A compound according to claim 1, wherein such compound is O-(N-methyl-N-phenyl-carbamoylmethyl)N'-dichloroacetyl-hydrazine-N-thiocarboxylate of the formula

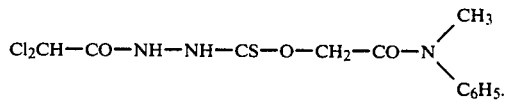

7. A compound according to claim 1, wherein such compound is O-(N-methyl-N-phenyl-carbamoylmethyl)N'-chloroacetyl-hydrazine-N-thiocarboxylate of the formula

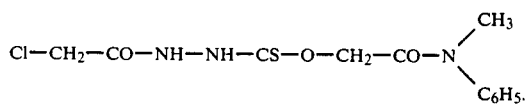

* * * * *